United States Patent
Gippetti et al.

(10) Patent No.: US 11,908,586 B2
(45) Date of Patent: Feb. 20, 2024

(54) SYSTEMS AND METHODS FOR EXTRACTING DATES ASSOCIATED WITH A PATIENT CONDITION

(71) Applicant: Flatiron Health, Inc., New York, NY (US)

(72) Inventors: James Gippetti, Bay Shore, NY (US); Sharang Phadke, Plainsboro, NJ (US); Guy Amster, Hoboken, NJ (US); Nisha Singh, South Richmond Hill, NY (US); Suganya Sridharma, Ashburn, VA (US); Melissa Estevez, Raleigh, NC (US); John Ritten, Brooklyn, NY (US); Sankeerth Garapati, New York, NY (US); Aaron Cohen, South Orange, NJ (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 17/345,448

(22) Filed: Jun. 11, 2021

(65) Prior Publication Data

US 2021/0391087 A1 Dec. 16, 2021

Related U.S. Application Data

(60) Provisional application No. 63/038,397, filed on Jun. 12, 2020.

(51) Int. Cl.
*G16H 50/70* (2018.01)
*G16H 40/20* (2018.01)
(Continued)

(52) U.S. Cl.
CPC ............. *G16H 50/70* (2018.01); *G06F 16/33* (2019.01); *G06N 20/00* (2019.01); *G16H 10/60* (2018.01); *G16H 40/20* (2018.01); *G16H 50/20* (2018.01)

(58) Field of Classification Search
CPC ........ G16H 50/70; G16H 40/20; G16H 10/60; G16H 50/20; G06F 16/33; G06N 20/00
See application file for complete search history.

(56) References Cited

U.S. PATENT DOCUMENTS

| 10,304,000 | B2 | 5/2019 | Birnbaum et al. | |
|---|---|---|---|---|
| 2008/0301122 | A1* | 12/2008 | Almeida ............... | G06Q 10/02 707/999.005 |

(Continued)

FOREIGN PATENT DOCUMENTS

WO  WO 2020/092316 A1   5/2020

OTHER PUBLICATIONS

International Search Report and Written Opinion issued in PCT Application No. PCT/US2021/036948 dated Sep. 23, 2021 (13 pages).

*Primary Examiner* — Fonya M Long
*Assistant Examiner* — Anthony Balaj
(74) *Attorney, Agent, or Firm* — Finnegan, Henderson, Farabow, Garrett & Dunner, LLP

(57) ABSTRACT

A model-assisted system for extracting patient information. A processor may be programmed to access a database storing one or more medical records associated with a patient and determine, using a first machine learning model and based on unstructured information included in the one or more medical records, whether the patient is associated with a condition. The processor may further be programmed to identify a date associated with the patient and determine, using a second machine learning model and based on the unstructured information, whether the patient is associated (Continued)

with the condition relative to the date. The processor may generate an output indicating whether the patient is associated with the condition and whether the patient is associated with the condition relative to the date.

16 Claims, 8 Drawing Sheets

(51) Int. Cl.
*G16H 10/60* (2018.01)
*G16H 50/20* (2018.01)
*G06F 16/33* (2019.01)
*G06N 20/00* (2019.01)

(56) References Cited

U.S. PATENT DOCUMENTS

| | | |
|---|---|---|
| 2016/0034642 A1* | 2/2016 | Ehrhart .................. G16H 10/60 705/3 |
| 2017/0039341 A1 | 2/2017 | Shklarski et al. |
| 2018/0089376 A1 | 3/2018 | Tucker et al. |
| 2018/0225680 A1* | 8/2018 | Wilson ............... G06Q 30/0201 |
| 2019/0131016 A1* | 5/2019 | Cohen ................... G16H 70/60 |
| 2020/0176098 A1* | 6/2020 | Lucas .................... G16H 10/60 |
| 2020/0211716 A1* | 7/2020 | Lefkofsky .............. G06N 20/00 |
| 2021/0027868 A1* | 1/2021 | McNeil .................. G16H 10/60 |
| 2021/0027894 A1 | 1/2021 | Rich et al. |
| 2021/0109915 A1* | 4/2021 | Godden ................ G16H 10/60 |

* cited by examiner

SYSTEMS AND METHODS FOR EXTRACTING DATES ASSOCIATED WITH A PATIENT CONDITION

CROSS REFERENCE TO RELATED APPLICATION

This application claims the benefit of priority of U.S. Provisional Application No. 63/038,397, filed on Jun. 12, 2020. The contents of the foregoing application are incorporated herein by reference in their entirety.

BACKGROUND

Technical Field

The present disclosure relates to identifying patient conditions and dates associated with those conditions in large sets of unstructured data and, more specifically, to the architecture of a deep learning model configured to determine attributes of the patient conditions.

Background Information

In today's health care system, access to patient diagnosis, treatment, testing, and other healthcare data across large populations of patients can provide helpful insights for understanding diseases and for developing new forms of therapies and treatments. For example, researchers may use data to assess patients' responses to particular treatments, understand differences in patient outcomes between patients with similar conditions, identify patients to include in a cohort for a treatment, or the like. As one example, researchers may be interested in data relating to sites of metastases for cancer patients. In particular, researchers may be interested in data relating to timings at which these metastases are diagnosed at different sites, especially relative to diagnoses and associated timing of relevant events and lines of therapy, etc.

This information may be included in electronic medical records (EMRs) for patients. Each medical record may include large amounts of data associated with a patient. Accordingly, processing these records to identify relevant information for statistically important sets of cohorts can quickly become an unsurmountable task for manual approaches. For example, researchers who wish to perform a statistical analysis on patient medical data often require relatively large data sets (e.g., thousands, tens of thousands, hundreds of thousands, or millions of patients, or more) in order to draw meaningful insights from the data. It is virtually impossible for human reviewers to process this volume of data. Accordingly, patient data gathered by manual data extracted by human reviewers typically results in small sets of patients, which may limit the efficacy of the data. Moreover, due to the limited size of the data set, rare conditions that occur only in a small percentage of patients may not be represented in the data set.

Accordingly, computer-based extraction of data from EMRS may be required to acquire statistically meaningful sets of data. However, relevant information in the EMRs may be stored in unstructured notes or various other forms of unstructured information (e.g., doctors' visit notes, lab technician reports, or other text-based data), which can make computer-based extraction of relevant information (e.g., information indicating sites of metastases, the dates of appearance of those metastases, etc.) difficult an impracticable without system capabilities for recognizing important and/or relevant information from sources that include unstructured information.

In view of these and other deficiencies in current techniques, technical solutions are needed for more accurately identifying patients with particular diagnoses, test results, or other characteristics relative to particular dates, such as dates when treatments or therapies begin. In particular, the solutions should allow for identification of metastatic sites and corresponding diagnosis dates for metastatic sites based on automatic analysis of very large sets of patient data.

SUMMARY

Embodiments consistent with the present disclosure include systems and methods for extracting patient information. In an embodiment, a model-assisted system may comprise at least one processor. The processor may be programmed to access a database storing one or more medical records associated with a patient; determine, using a first machine learning model and based on unstructured information included in the one or more medical records, whether the patient is associated with a condition; identify a date associated with the patient; determine, using a second machine learning motel and based on the unstructured information, whether the patient is associated with the condition relative to the date; and generate an output indicating whether the patient is associated with the condition and whether the patient is associated with the condition relative to the date.

In another embodiment, a computer-implemented method for extracting patient information is disclosed. The method may comprise accessing a database storing one or more medical records associated with a patient; determining, using a first machine learning model and based on unstructured information included in the one or more medical records, whether the patient is associated with a condition; identifying a date associated with the patient; determining, using a second machine learning model and based on the unstructured information, whether the patient is associated with the condition relative to the date; and generating an output indicating whether the patient is associated with the condition and whether the patient is associated with the condition relative to the date.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings.

DETAILED DESCRIPTION

Figure 1:
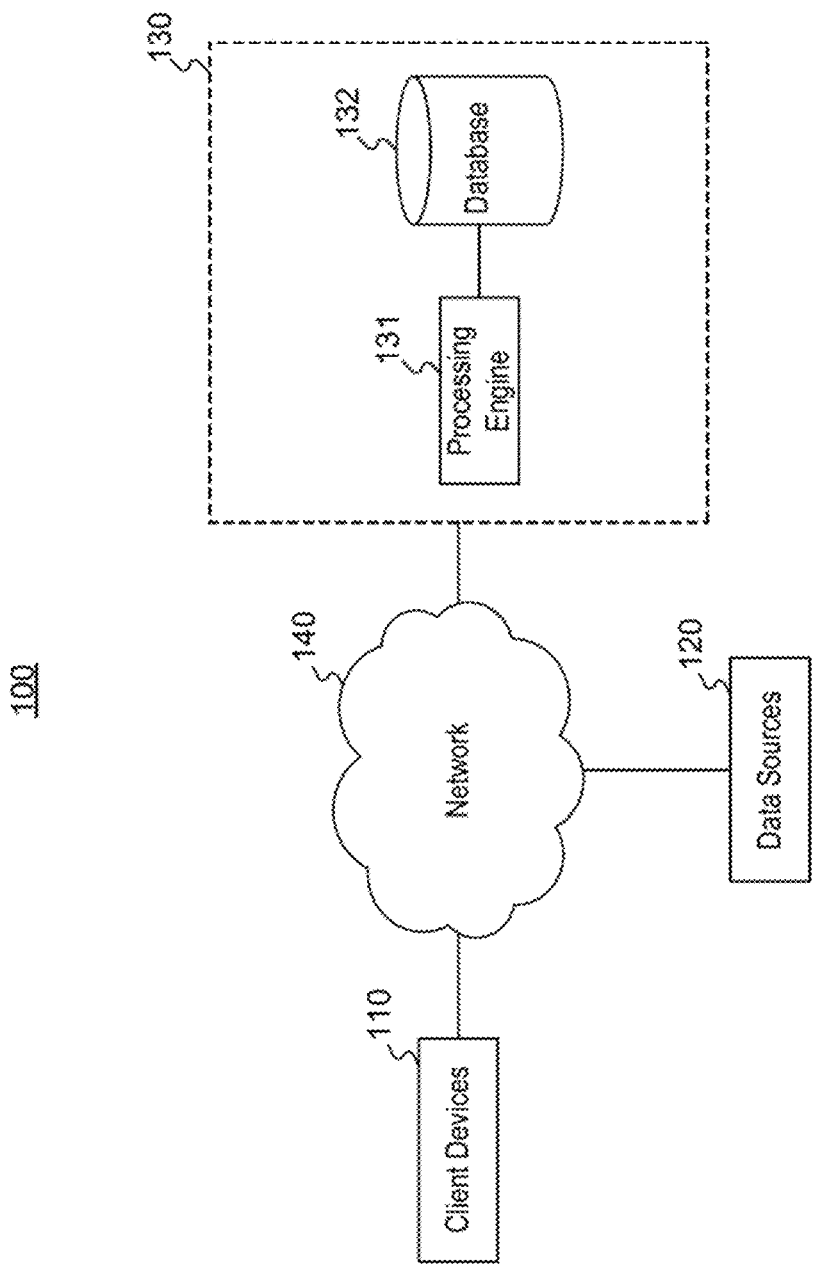
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a ion-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

The disclosed embodiments may automate the analysis of medical records of a patient or patient population to identify characteristics of the patients relative to one or more dates of clinical relevance. For example, researchers, physicians, or other users may be interested in identifying patients diagnosed with a brain metastasis (or various other sites of metastases) relative to one or more lines of therapy provided to the patient. This may provide insights into, among other things, how effective a particular line of therapy is. For example, if a patient is administered three different cancer treatment therapies, researchers may be interested in determining when and where different metastases appeared relative to the start and end dates of these treatments. This may indicate how well a patient or group of patients has responded to certain therapies. Accordingly, the disclosed embodiments may allow for generation of large patient cohorts relevant to a metastatic site based on analysis of medical records. In particular, the system may automatically analyze patient medical records (including unstructured patient data) to identify large cohorts of patients (e.g., up to millions of patients or more) that exhibit a certain type of metastasis or that exhibit certain types of metastases along with certain lines of therapies. Additional techniques for selecting cohorts are described in detail in U.S. Pat. No. 10,304,000 and PCT International Patent Publication No. WO 2020/092316 (and corresponding U.S. patent application Ser. No. 16/971,238) assigned to the same applicant as the present application, which are hereby incorporated by reference herein in their entirety.

Once this initial cohort has been identified, the system may further filter the cohort based on other patient characteristics. In particular, the system may automatically make determinations associated with metastatic sites, dates these metastases were diagnosed, and relationships between these dates and metastatic sites with other dates or characteristics, such as patient treatment dates. For example, the system may identify patients having a brain metastasis that were provided a particular therapy, patients who have been diagnosed with the brain metastasis at a particular range of times relative to the particular therapy, or the like. While diagnosis of brain and other metastatic sites are used throughout the present disclosure by way of example, the disclosed techniques may apply to other patient conditions, such as other sites of metastasis, other diagnosis types, test results (e.g., PDL1 genetic mutation testing, etc.), lab results, or various conditions or events that may be represented in a patient medical record.

FIG. 1 illustrates an example system environment 100 for implementing embodiments consistent with the present disclosure, described in detail below. As shown in FIG. 1, system environment 100 may include several components, including client devices 110, data sources 120, system 130, and/or network 140. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 may include a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processing engine 131 and one or more databases 132, which are illustrated in a region bounded by a dashed line representing system 130. Processing engine 131 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse. A user of environment 100 may encompass any individual who may wish to access and/or analyze patient data. Thus, throughout this disclosure, references to a "user" of the disclosed embodiments may encompass any individual, such as a physician, a researcher, a quality assurance department at a health care institution, and/or any other individual.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

The components of environment 100 (including system 130, client devices 110, and data sources 120) may communicate with each other or with other components through a network 140. Network 140 may comprise various types of networks, such as the Internet, a wired Wide Area Network (WAN), a wired Local Area Network (LAN), a wireless WAN (e.g., WiMAX), a wireless LAN (e.g., IEEE 802.11, etc.), a mesh network, a mobile/cellular network, an enterprise or private data network, a storage area network, a virtual private network using a public network, a nearfield communications technique (e.g., Bluetooth, infrared, etc.), or various other types of network communications. In some embodiments, the communications may take place across two or more of these forms of networks and protocols.

System 130 may be configured to receive and store the data transmitted over network 140 from various data sources, including data sources 120, process the received data, and transmit data and results based on the processing to client device 110. For example, system 130 may be configured to receive patient data from data sources 120 or other sources in network 140. In some embodiments, the patient data may include medical information stored in the form of one or more medical records. Each medical record may be associated with a particular patient. Data sources 120 may be associated with a variety of sources of medical information for a patient. For example, data sources 120 may include medical care providers of the patient, such as physicians, nurses, specialists, consultants, hospitals, clinics, and the like. Data sources 120 may also be associated with laboratories such as radiology or other imaging labs, hematology labs, pathology labs, etc. Data sources 120 may also be associated with insurance companies or any other sources of patient data.

System 130 may further communicate with one or more client devices 110 over network 140. For example, system 130 may provide results based on analysis of information from data sources 120 to client device 110. Client device 110 may include any entity or device capable of receiving or transmitting data over network 140. For example, client device 110 may include a computing device, such as a server or a desktop or laptop computer. Client device 110 may also include other devices, such as a mobile device, a tablet, a wearable device (i.e., smart watches, implantable devices, fitness trackers, etc.), a virtual machine, an IoT device, or other various technologies. In some embodiments, client device 110 may transmit queries for information about one or more patients over network 140 to system 130, such as a query for patients having or being associated with a particular attribute, patients associated with a particular attribute in reference to a specified date, or various other information about a patient.

In some embodiments, system 133 may be configured to analyze patient medical records (or other forms of unstructured data) to determine whether a patient is associated with a particular condition. For example, system 130 may analyze medical records of a patient to determine whether the patient has been diagnosed with a particular condition (e.g., metastasis in a particular region of the body), undergone testing for a particular condition, tested positive or negative for a particular condition, or various other characteristics. System 130 may further be configured to determine whether the patient exhibits a particular condition in reference to a date. For example, system 130 may determine whether a patient exhibits a particular condition prior to a start date or end date of a line of treatment, or other dates that may be of interest. System 130 may be configured to use one or more machine learning models to perform this analysis, as described further below. While patient medical records are used as an illustrative example throughout the present disclosure, it is understood that in some embodiments, the disclosed systems, methods, and/or techniques may similarly be used for identifying patients exhibiting conditions from other forms of records.

Figure 2:
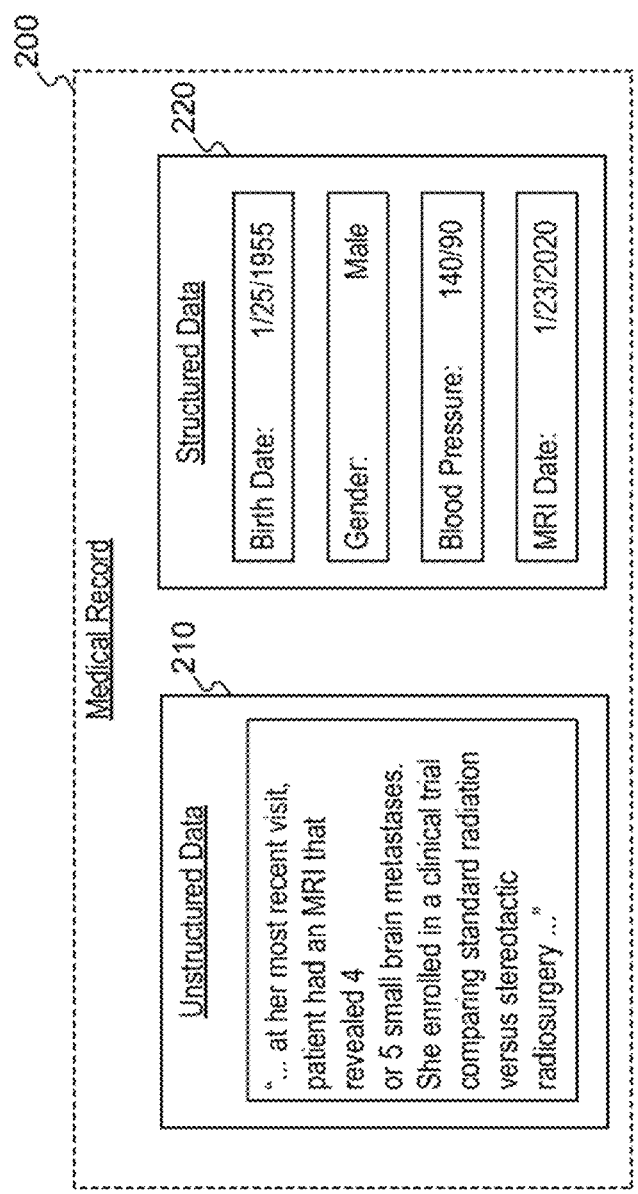
FIG. 2 is a block diagram illustrating an exemplary medical record for a patient, consistent with the disclosed embodiments.

FIG. 2 is a block diagram illustrating an exemplary medical record 200 for a patient, consistent with the disclosed embodiments. Medical record 200 may be received from data sources 120 and processed by system 130 to identify whether a patient is associated with particular attributes, as described above. The records received from data sources 120 (or elsewhere) may include one or both of unstructured data 210 and structured data 220, as shown in FIG. 2. Structured data 220 may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient.

As described above, much of the information relative to making determinations about a patient, such as whether the patient has been diagnosed with a particular condition, dates of diagnosis, and other similar information, may be stored in unstructured data of a patient medical record. As used herein, unstructured data may include information about the patient that is not quantifiable or easily classified, such as physician's notes or the patient's lab reports. For example, unstructured data 210 may include information such as a physician's description of a treatment plan, notes describing what happened at a visit, statements or accounts from a patient, subjective evaluations or descriptions of a patient's well-being, radiology reports, pathology reports, or any other forms of information not stored in a structured format.

In the data received from data sources 120, each patient may be represented by one or more records generated by one or more health care professionals or by the patient. For example, a doctor associated with the patient, a nurse associated with the patient, a physical therapist associated with the patient, or the like, may each generate a medical record for the patient. In some embodiments, one or more records may be collated and/or stored in the same database. In other embodiments, one or more records may be distributed across a plurality of databases. In some embodiments, the records may be stored and/or provided a plurality of electronic data representations. For example, the patient records may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, the unstructured data may be captured by an extraction process, while the structured data may be entered by the health care professional or calculated using algorithms.

In some embodiments, the unstructured data may include data associated with particular patient conditions. As used herein, a "condition" of a patient may refer to any attribute or characteristic associated with the health or wellbeing of a patient. For example, the condition may refer to a diagnosed condition of a patient, such as whether the patient has been diagnosed with a particular illness or disease. In some embodiments, the condition may refer to a stage or status of a particular diagnosed condition. For example, for a patient diagnosed with cancer, the condition may be a particular site of metastasis of the cancer (e.g., whether the patient has been diagnosed with metastasis in the brain, liver, bones, lungs, adrenal gland, peritoneum, or various other sites of metastases). While sites of metastases are used by way of example throughout the present disclosure, it is to be understood that the disclosed embodiments and techniques may equally apply to other conditions and that the present disclosure is not limited to any particular condition.

Whether a patient is associated with a condition of interest, as well as whether the condition is observed by a particular date, may be extracted from unstructured data 210. As an example, the condition may include metastasis in the brain and system 130 may analyze patient medical records to determine whether a patient has been diagnosed with brain metastasis. In some embodiments, this extraction may occur through the implementation of one or more trained models. For example, the one or more models (e.g., one or more machine learning model) may be trained to identify documents, such as patient medical records, indicating a patient has been diagnosed with a brain metastasis, and whether the brain metastasis developed relative to one or more dates (e.g., before or after a date of interest).

Various types of dates may be analyzed in reference to a patient condition. These dates of interest may vary depending on a particular application, such as a type of cohort being selected, a type of research, a type of condition being analyzed, or various other factors. The date or dates may be specified in a variety of ways. In some embodiments, a user interface may be provided such that a user may input a reference date to identify patients diagnosed with a certain condition prior to that date. For example, a user interface may be presented on one or more client devices 110. Alternatively, or additionally, the date may be identified in reference to another date associated with diagnosis, treatment, or other aspects of a patient's care. For example, the date may be a start or end date of a particular line of treatment or therapy for a patient. As used herein, a line of therapy (or line of treatment) may refer to a therapy employed to treat a particular disease or condition. For example, a line of therapy may include administration of a particular drug to a patient (e.g., pharmacotherapy, chemotherapy, etc.), a surgical procedure, a gene therapy, an immunotherapy, changes to a patient's diet, radiation therapy, physiotherapy, counseling or psychotherapy, meditation, sleep therapy, or various other forms of treatment that may be prescribed for a patient. In some embodiments, the date may be an index date defining inclusion criteria for a cohort. For example, researchers or other users may define a date such that patients exhibiting a condition in reference to an index date are eligible for inclusion in a study.

In some embodiments, multiple dates may be specified. For example, a patient may undergo multiple lines of therapy and development of a condition may be analyzed with respect to one or more line of therapy. Accordingly, for each condition of a patient, a timeline may be developed indicating a list of dates with indicators of whether the condition had developed prior to the dates. For example, these dates may include an advanced diagnosis date, a date a patient began a first line of therapy, a date the patient ended a first line of therapy, a date the patient began a second line of therapy, a date the patient ended a second line of therapy, and so on. The model may output a table or similar data structure indicating whether the condition had been diagnosed prior to these dates. This process may be performed across a pool of patient data to extract information that may be statistically robust tor researchers.

Figure 3:
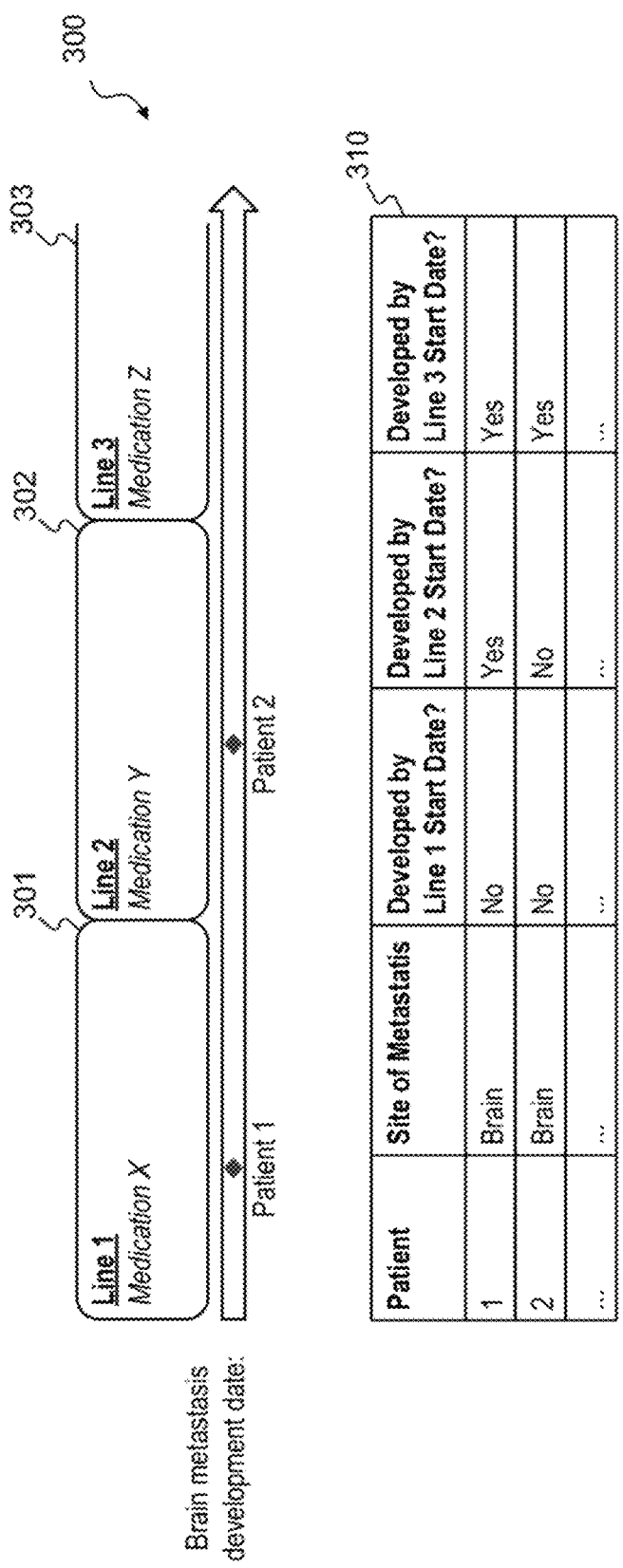
FIG. 3 illustrates an example timeline illustrating multiple lines of therapy associated with a patient, consistent with the disclosed embodiments.

FIG. 3 illustrates an example timeline 300 illustrating multiple lines of therapy associated with a patient, consistent with the disclosed embodiments. For example, one or more patients may undergo a first line of therapy 301 in which they are treated with "Medication X," a second line of therapy 302 in which they are treated with "Medication Y," and a third line of therapy 303 in which they are treated with "Medication Z." As shown in timeline 300, first patient ("Patient 1") may develop metastasis in the brain during line of therapy 301, while a second patient ("Patient 2") may develop metastasis in the brain during line of therapy 302.

System 130 may be configured to analyze medical records associated with Patient 1 and Patient 2 to determine that Patient 1 and Patient 2 have been diagnosed with metastasis of the brain. System 130 may further determine whether the brain metastases for Patient 1 and Patient 2 developed relative to the start dates of each of lines of therapy 301, 302, and 303. For example, system 130 may generate an output 310 indicating that Patient 1 was diagnosed with brain metastasis that had not developed by the start date for line of therapy 301, but that did develop by the start date of lines of therapy 302 and 303. This may provide insight, for example, to physicians, researchers, or other users as to the efficacy of lines of therapy 301, 302, and/or 303. In some embodiments, output 310 may provide information for multiple patients. For example, as shown in FIG. 3, output 310 may indicate that Patient 2 also exhibits metastasis in the brain that had not developed prior to the start of lines of therapy 301 and 302, but that did develop prior to the start of line of therapy 303. Output 310 may include similar information for a larger group of patients. Accordingly, patients may be selected for a cohort or otherwise analyzed based on whether they have been diagnosed with brain metastasis or whether the condition has developed relative to one or more dates.

In some embodiments, this process may use two or more separately trained models (e.g., two or more separate machine learning models). For example, a first machine learning model may be trained to identify patients having been diagnosed with the metastasis site of interest. A second machine learning model may then be trained to determine other information, such as a metastasis type, a metastasis location, a date the metastasis appeared or was diagnosed, types of treatments the patient received, dates of these treatments, and other information that may be relevant. Based on this information, researchers may use the disclosed system and method to identify patients having certain characteristics, such as whether the metastasis was developed prior to one or more dates. As described above, these dates may correspond to line of therapy dates associated with a patient, such as the dates a particular treatment began or ended. Accordingly, a researcher may identify a patient having metastasis diagnosis dates relative to these lines of therapy, which may provide insight into the patient's reactions to these therapies or similar insights.

Figure 4:
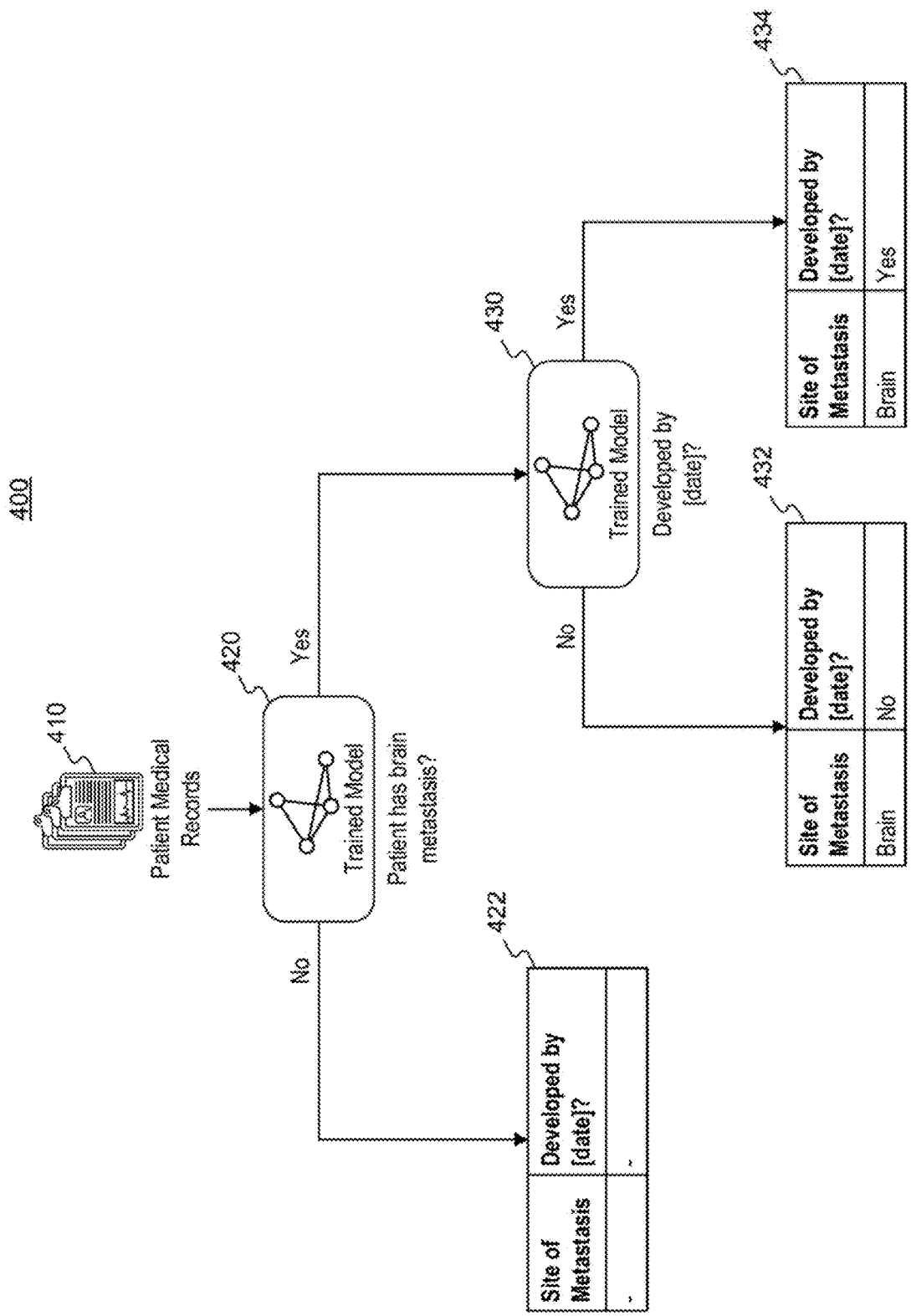
FIG. 4 is an example block diagram illustrating a process for extracting patient information relative to one or more dates, consistent with the disclosed embodiments.

FIG. 4 is an example block diagram illustrating a process 400 for extracting patient information relative to one or more dates, consistent with the disclosed embodiments. Process 400 may be performed based on a group of medical records 410. In some embodiments, medical records 410 may be associated with a particular patient. Accordingly, process 400 may be used to determine whether the patient has been diagnosed with metastasis of the brain, and whether the metastasis was developed before or after a specified date. Alternatively, or additionally, medical records 410 may be associated with a plurality of patients. Accordingly, process 400 may be used to identify patients that have been diagnosed with metastasis of the brain, and further, which patients developed the metastasis in the brain before or after a specified date. Accordingly, the process 400 may allow for analysis of large groups of patient medical records (including unstructured patient data) to identify cohorts of patients that exhibit a certain type of metastasis or that exhibit certain types of metastases and whether the metastases were developed before beginning certain lines of therapies or other dates of interest. While metastasis in the brain is used by way of example, process 400 may equally apply to other sites of metastases or other conditions.

Medical records 410 may be input into a first trained model 420. Trained model 420 may be configured to identify patients having been diagnosed with a metastasis in a particular site, such as a brain metastasis. For example, a training algorithm, such as an artificial neural network may receive training data in the form of unstructured data from medical records. The training data may be labeled to indicate particular conditions that patients associated with the unstructured data have been diagnosed with. As a result, a model may be trained to determine conditions, such as whether a patient has been diagnosed with brain metastasis, based on unstructured data in patient medical records. Consistent with the present disclosure, various other machine learning algorithms may be used, including a logistic regression, a linear regression, a regression, a random forest, a K-Nearest Neighbor (KNN) model (for example as described above), a K-Means model, a decision tree, a cox proportional hazards regression model, a Naïve Bayes model, a Support Vector Machines (SVM) model, a gradient boosting algorithm, or any other form of machine learning model or algorithm. An example training process is described in greater detail below with respect to FIG. 5.

As shown in FIG. 4, trained model 420 may determine, for each patient, whether the patient has been diagnosed with brain metastasis (or various other conditions). If not, an output 422 may indicate that no metastasis in the brain is associated with the patient. On the other hand, if trained model 420 does determine the patient has been diagnosed with brain metastasis, data associated with the patient may be input into a second trained model 430, as shown. In embodiments where medical records 310 include a large set of patients, the trained model 420 may therefore filter out patients (and patient medical records) that do not include the specified condition. In some embodiments, documents identified as being relevant to the condition by trained model 420 may be selected for input into trained model 430. Accordingly, including trained model 420 may allow for more efficient application of trained model 430.

Trained model 430 may extract information for further narrowing the set of documents. For example, trained model 430 may allow researchers to identify patients in which a particular condition had been diagnosed by certain dates, as described above. Similar to trained model 420, trained model 430 may be trained based on a training data set of documents known to include diagnoses for a particular condition, along with diagnosis dates for the condition. As a result, the second model may be trained to indicate the dates at which a relevant diagnosis has been made. A similar training process may be applied for determining lines of treatment, start dates for the line of treatment, etc.

As a result, trained model 430 may determine, for each patient, whether the patient has been diagnosed with brain metastasis (or various other conditions) by a certain date. For example, the date may be a start date for a particular line of therapy, or various other dates that may be of interest. If not, an output 432 may indicate that metastasis in the brain has been diagnosed but that it has not been developed by the date in question. If the patient has developed metastasis in the brain by the specified date, this may be reflected in output 434. In some embodiments, trained model 430 may determine whether the patient condition has been developed with respect to multiple dates, as shown in FIG. 3. Alternatively, or additionally, trained model 430 may include multiple trained models, each of which may determine whether the patient developed the condition by a different date. In embodiments where medical records 310 include a large set of patients, models 420 and 430 may be used to narrow the set of patients to identify only those that have developed a condition in relation to a specified date. Accordingly, process 400 may be used for selecting patients for a cohort or otherwise identifying a particular subgroup of patients. While the description above refers to a process performed by two separate models, in some embodiments, this process may be performed by a single model, or may be performed by more than two models.

Figure 5:
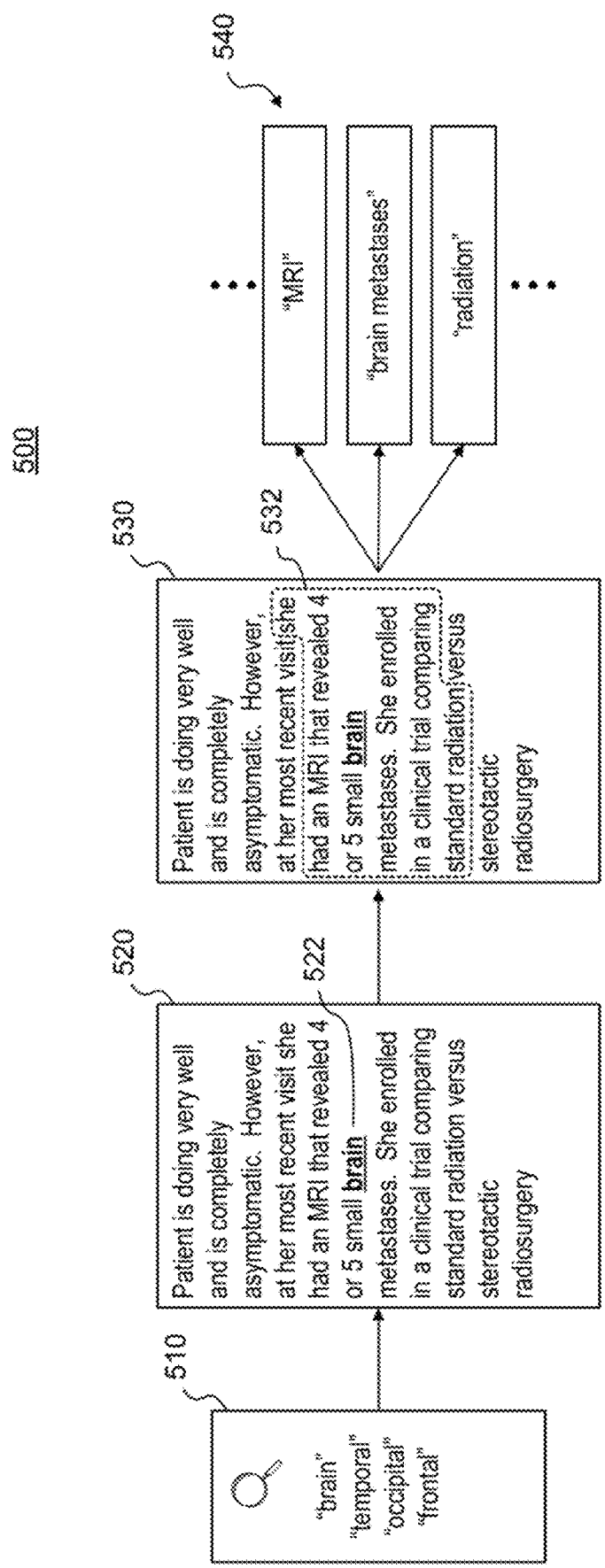
FIG. 5 illustrates an example process for extracting features based on snippets of text in unstructured data of patient medical records, consistent with the disclosed embodiments.

FIG. 5 illustrates an example process 500 for extracting features based on snippets of text in unstructured data of patient medical records, consistent with the disclosed embodiments. As discussed above, trained model 420 may be configured to determine whether a patient exhibits a particular condition. In some embodiments, system 130 may perform a search on a set of training documents (which may be a set of patient medical records) known to include information regarding diagnosis of a particular condition to extract features that may be input into a model, such as a logistic regression algorithm. For example, system 130 may perform a search 510 on one or more unstructured medical record documents to extract snippets associated with a patient condition. In the case of a brain metastasis, the relevant terms may include "brain," "temporal," "occipital," "frontal," or other terms that may be commonly associated with the brain. Accordingly, system 130 may identify term 522 as shown in step 520. System 130 may then extract snippets of text surrounding the relevant terms in the unstructured data. For example, as shown in step 530, snippet 532 surrounding term 522 may be extracted from the unstructured text. The length or structure of the snippet may be specified in various ways. In some embodiments, snippet 532 may be defined based on a predefined window. For example, the snippet may be defined based on a predetermined number of characters before and after target term 522 in the text (e.g., 20 characters, 50 characters, 60 characters, or any suitable number of characters to capture context for use of the term). The window may also be defined to respect word boundaries such that partial words are not included in the edges of the snippet, for example, by expanding or narrowing the window to end at word boundaries. In some embodiments, the window may be defined based on a predefined number of words, or other variables.

In some embodiments, system 133 may replace term 522 with a tokenized term. This may ensure that the patient condition is expressed using the same terminology in each of the extracted snippets. For example, documents including "brain" and documents including "cerebrum" may both result in extracted snippets including the term "[_brain_]," or a similar token. The use of a token may also improve performance of a machine learning model by reducing feature sparsity, speeding up training time, and allowing the model to converge with more limited sets of labeled data.

Next, the system may extract other words or phrases from within the snippet that may be relevant to identifying diagnosis information in the document. These words or phrases may be represented as features 540 shown in FIG. 5. For example, the snippets may include the terms "MRI," "metastasis," "metastases," "lesion," and "radiation." For each of these terms (or phrases), features may be generated, which may be input into a regularized logistic expression to determine relative weights for each of the features. Accordingly, a model may be generated and trained that identifies documents including a brain metastasis diagnosis. While process 500 illustrates a general overview of a process for extracting feature vectors for purposes of determining whether a patient is associated with a particular condition, various other techniques may be used. Examples of machine learning techniques for determining whether a patient is associated with a particular characteristic are described in detail in U.S. Patent Publication No. 2021/0027894 A1 and PCT International Publication No. WO 2020/092316, which are assigned to the same applicant as the present application. The contents of these applications are hereby incorporated by reference herein in their entirety.

In some embodiments, inconsistencies in the way diagnoses are represented in the unstructured data may make it difficult to determine diagnosis dates in some instances. For example, a physician may include a note indicating a brain metastasis was observed "one month ago" or "3 months after [line of treatment] began." To account for this, the documents input into trained model 430 may be limited and/or modified to improve the accuracy of determining patient conditions relative to one or more dates.

Figure 6A:
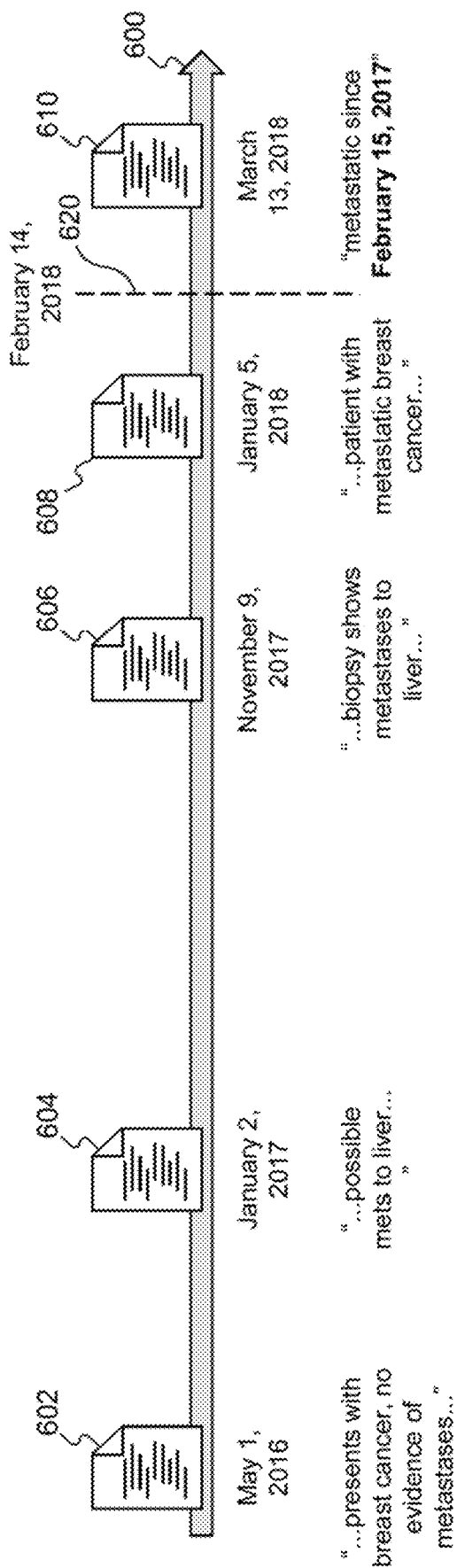
FIG. 6A illustrates an example set of documents that may be analyzed to determine whether a patient condition is present relative to a date, consistent with the disclosed embodiments.

FIG. 6A illustrates an example set of documents that may be analyzed to determine whether a patient condition is present relative to a date, consistent with the disclosed embodiments. A set of documents 602, 604, 606, 608, and 610 may be analyzed to determine whether a patient has developed a liver metastasis before a particular date 620. Each of documents 602, 604, 606, 608, and 610 may be associated with a document date. The document date may refer to a date the document was created and may be extracted from metadata or other data associated with the document. The document date may refer to various other dates associated with the document, such as a date the document was updated, a revision date, a filing date, a publication date, or any other relevant date. For example, document 602 may be associated with a date of May 1, 2016. For purposes of illustration, documents 602, 604, 606, 608, and 610 are shown along a timeline 600 corresponding to the document date for each document. Researchers may be interested in determining whether metastasis of the liver developed before date 620—in this case, Feb. 14, 2018.

Documents 602, 604, 606, 608, and 610 may each contain text relevant to when metastasis in the liver has developed. Accordingly, there may be references to an event both before and after it occurs. Further, explicit dates may not be present, but unstructured text data may indicate various stages of the development. For example, document 602 may indicate that the patient is a breast cancer patient and that no metastasis in the liver (or at other potential sites of metastases) has developed. Documents 606 and 608, may indicate that metastasis to the liver has been diagnosed and thus the metastasis developed prior to those dates. For each document, trained model 430 may predict a probability of whether the condition developed before, after, or equal to date 620.

In some instances, as described above, dates may be expressed in relative terms. For example, a document may indicate that metastasis of the liver developed relative to another event (e.g., beginning a line of treatment). In the example shown in FIG. 6A, document 610 may include an explicit date at which metastasis of the liver was developed. However, other documents may express the date in relevant terms, such as "3 months ago" or the like. The inclusion of these documents expressing relative dates may introduce error or inaccuracies into the determination whether a condition developed prior to a date. For example, trained model 430 may not properly interpret the relative language used, which may skew the analysis.

Figure 6B:
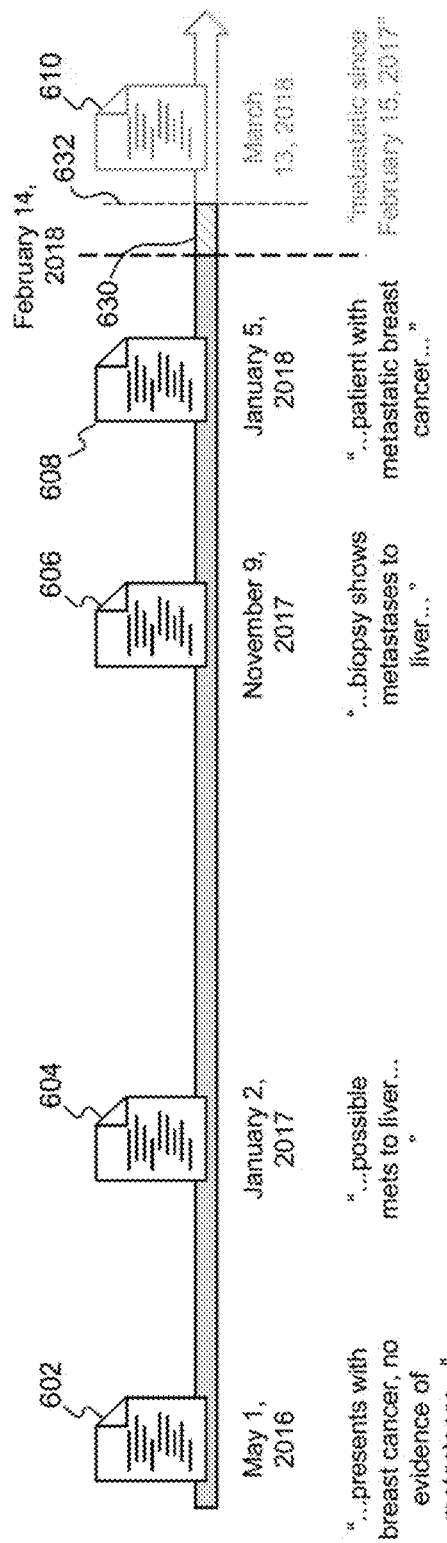
FIGS. 6B and 6C illustrate example techniques for analyzing the set of documents of FIG. 6A, consistent with the disclosed embodiments.

Accordingly, trained model 430 may consider only documents associated with a document date prior to date 620. FIG. 6B illustrates an example limited set of documents for input into a model, consistent with the disclosed embodiments. In particular, a cutoff date 632 may be specified such that documents after cutoff date 632 are not analyzed with respect to trained model 430. In the example shown in FIG. 6B, document 610 may be excluded from the documents input into trained model 430. In some embodiments, cutoff date 632 may be the same as date 620. This may mitigate issues associated with ambiguous descriptions of diagnosis dates in the unstructured data by focusing only on documents prior to the reference date. In some embodiments, a buffer 630 may also be applied such that cutoff date 632 is before or after date 620. For example, buffer 630 may be a buffer of 1 day, 7 days, 2 weeks, or any other suitable time period after date 620. This may ensure documents dated just after the reference date that may still contain relevant information are not excluded from analysis.

Figure 6C:
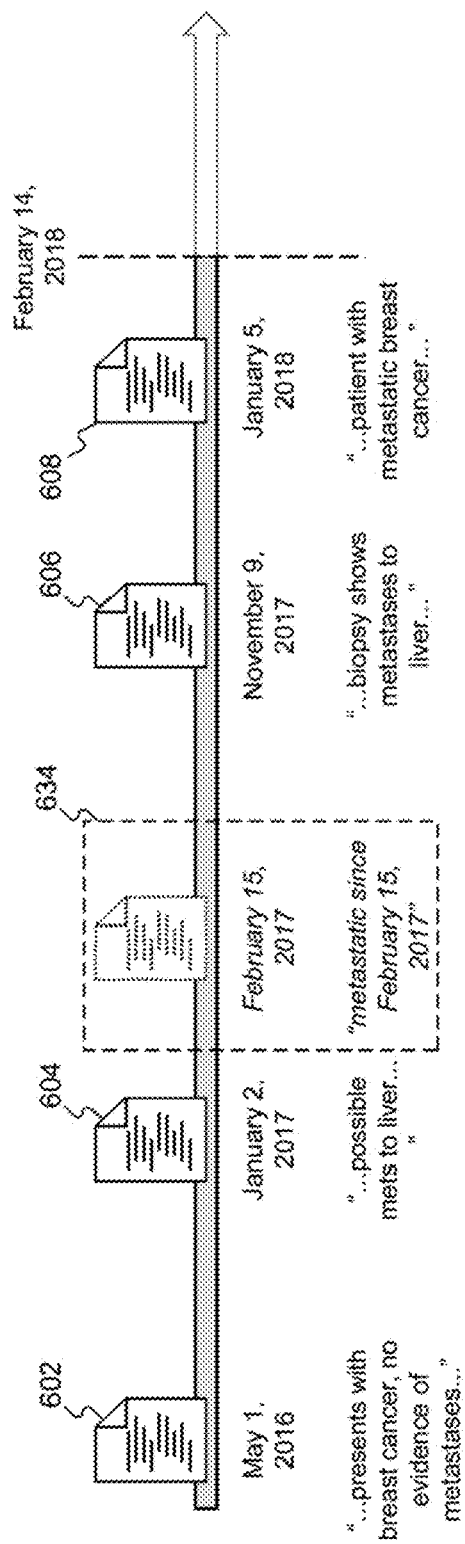

In some embodiments, system 133 may be configured to generate one or more "pseudo-documents" for input into trained model 430. By applying cutoff date 632, as discussed above, trained model 430 may miss explicit dates in the document text that may provide an accurate indication of when a condition develops. For example, as shown in FIG. 6B, trained model 430 may not be used to analyze document 610, which may indicate the metastasis of the liver developed on or around Feb. 17, 2017. To account for this, system 130 may generate a pseudo-document 634, as shown in FIG. 6C. The pseudo-documents may contain text of the original document but may be associated with a document date included in the text. For example, pseudo-document 634 may include the text from document 610 that mentions an explicit date but may be associated with a document date matching the explicit date, in this ease Feb. 15, 2017. Accordingly, the pseudo-documents may include the sentences explicitly indicating a date as though the sentence was written on that date. This may provide improved accuracy for determining whether the patient condition was developed prior to date 620 based on documents 602, 604, 606, 608, and 610.

Based on the disclosed techniques, the data regarding diagnoses and diagnosis dates may be extracted from patient medical records. In particular, such data may be extracted from unstructured data within the medical records, which may provide relatively large and statistically strong sets of data. Further, the diagnosis dates for various conditions may be compared to other key dates associated with one or more lines of therapy for the patient. This may allow researchers or other users to identify patients exhibiting certain responses to treatments (e.g., for cohort selection), compare the relative effectiveness of one or more treatments, or various other forms of analysis.

Figure 7:
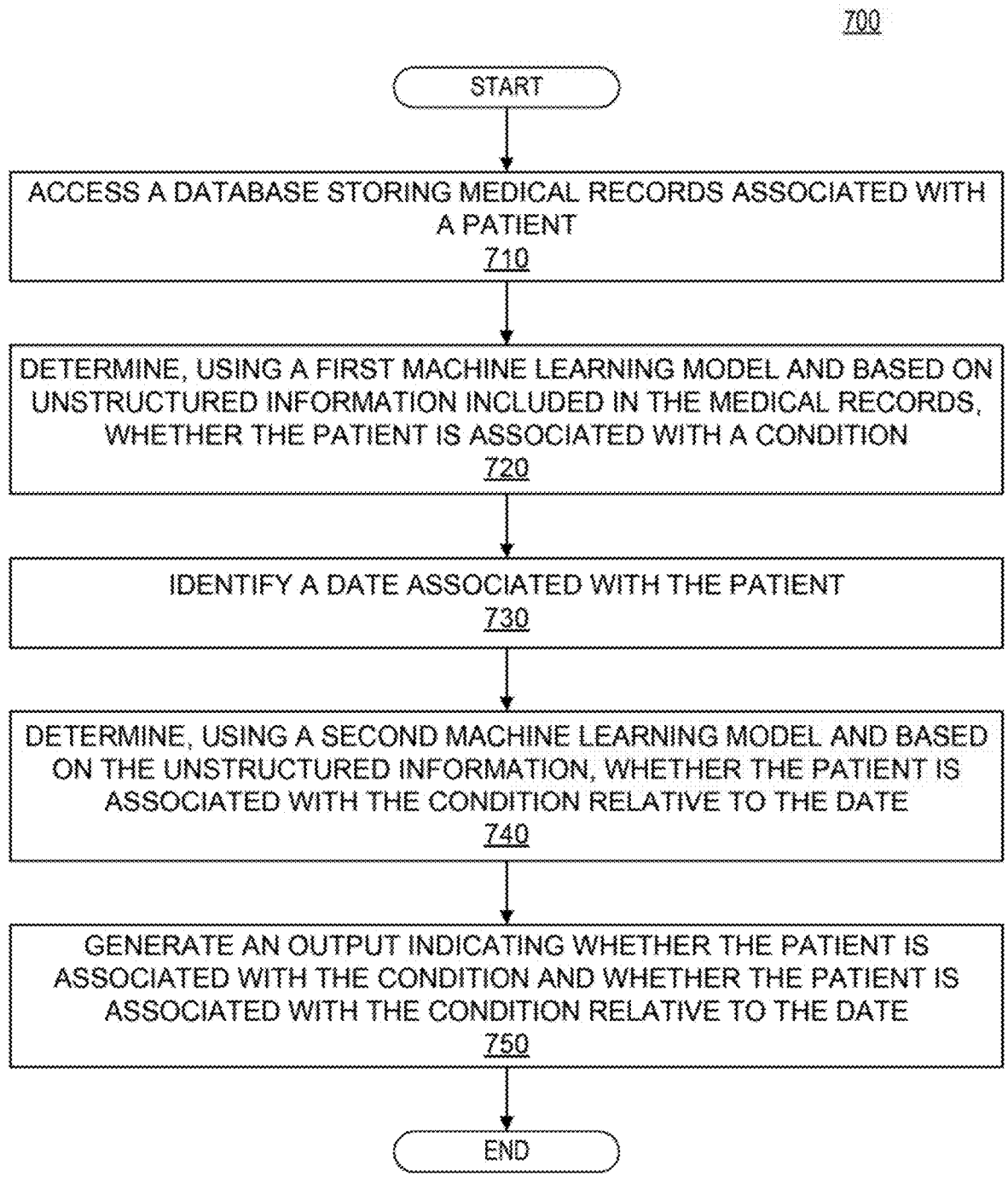
FIG. 7 is a flowchart showing an example process for extracting patient information, consistent with the disclosed embodiments.

FIG. 7 is a flowchart showing an example process 700 for extracting patient information, consistent with the disclosed embodiments. Process 700 may be performed by at least one processing device, such as processing engine 131, as described above. It is to be understood that throughout the present disclosure, the term "processor" is used as a shorthand for "at least one processor." In other words, a processor may include one or more structures that perform logic operations whether such structures are collocated, connected, or disbursed. In some embodiments, a non-transitory computer readable medium may contain instructions that when executed by a processor cause the processor to perform process 700. Further, process 700 is not necessarily limited to the steps shown in FIG. 7, and any steps or processes of the various embodiments described throughout the present disclosure may also be included in process 700, including those described above with respect to FIGS. 3, 4, 5, 6A, and 6B.

In step 710, process 700 includes accessing a database storing one or more medical records associated with a patient. For example, system 130 may access patient medical records from local database 132 or from an external data source, such as data sources 120. The medical record may comprise one or more electronic files, such as text files, image files, PDF files, XLM files, YAML files, or the like. The one or more medical records may correspond to medical record 200 discussed above.

In step 720, process 700 includes determining whether the patient is associated with a condition. In some embodiments, the condition may include a diagnosed condition of the patient, as described above. For example, the condition may include a diagnosed metastatic site associated with the patient, such as a brain metastasis. As another example, the condition may include whether a patient has been tested for a condition. The determination in step 720 may be made using a first machine learning model, such as trained model 420, described above. The determination in step 720 may be based on unstructured information included in the one or more medical records. For example, this may include unstructured data 210, as shown in FIG. 2 and described above. The unstructured information may include text written by a health care provider, a radiology report, a pathology report, or various other forms of text associated with the patient. In some embodiments the medical record may further include additional structured data 220.

In step 730, process 700 includes identifying a date associated with the patient. For example, the date may correspond to date 620 described above. This date may be determined in various ways. In some embodiments, step 730 may include receiving an indication of the date through a user interface, such as a user interface of computing devices 110. In some embodiments, the date may be determined based on one or more dates relevant to the care of the patient. For example, step 730 may include identifying at least one of a start date or an end date for a line of treatment for the patient in association with the condition.

In step 740, process 700 includes determining whether the patient is associated with the condition relative to the date. For example, this may include determining whether the patient developed the condition before or after the date. In some embodiments, the determination in step 740 may made using a second machine learning model, such as trained model 430. Alternatively, or additionally, a single model or more than two models may be used for steps 730 and 740. In some embodiments, multiple dates may be used. For example, step 730 may include identifying a plurality of dates, and step 740 may include determining whether the patient is associated with the condition includes determining whether the patient is associated with the condition relative to each of the plurality of dates. For example, as described above with respect to FIG. 3, the plurality of dates may each include a start dates for a particular line of treatment for the patient in association with the condition and step 740 may include determining whether the condition developed prior to the start dates for each line of treatment.

In some embodiments, step 740 may include applying the second machine learning model to documents having a timestamp before a cutoff date, as described above with respect to FIG. 6B. For example, step 740 may include identifying, within the one or more medical records, a plurality of documents having a timestamp prior to a cutoff date. Accordingly, determining whether the patient is associated with the condition relative to the date may include applying the second machine learning model to the plurality of documents. In some embodiments, the cutoff date may be the date. Alternatively, or additionally, the cutoff date may be based on a predetermined buffer period before or after the date. For example, cutoff date 632 may be determined based on buffer 630 relative to date 620, as described above.

In step 750, process 700 includes generating an output indicating whether the patient is associated with the condition and whether the patient is associated with the condition relative to the date. For example, this may include generating one of outputs 310, 422, 432, and/or 434, as described above. In some embodiments, process 750 may include transmitting the output to at least one of a healthcare provider or a research entity.

As described above, process 700 may be performed relative to a plurality of patients to identify a group of patients associated with the condition relative to the date. This may help researchers or healthcare providers select patients for a cohort, such as a cohort for inclusion in a study, for receipt of a particular treatment, or the like. Accordingly, process 700 may include determining, using the first machine learning model and based on the unstructured information, whether each of the plurality of patients is associated with the condition and determining using the second machine learning model and based on the unstructured information, whether each of the plurality of patients is associated with the condition relative to the date. Accordingly, the output may identify a group of the plurality of patients associated with the condition relative to the date.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic. C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps, it is intended, therefore, that the specification and examples be considered as illustrative only, with a true scope and spirit being indicated by the following claims and their full scope of equivalents.

What is claimed is:

1. A model-assisted system for extracting patient information, the system comprising:
at least one processor programmed to:
access a database storing a plurality of medical records associated with a plurality of patients;
input unstructured information included in the plurality of medical records into a first machine learning model, the first machine learning model being trained using first training data to identify patients associated with a condition;
identify, based on a first output from the first machine learning model, a subset of the plurality of patients, the subset of the plurality of patients being associated with the condition;
identify, based on an input by a user through a user interface, a date associated with a patient of the subset of the plurality of patients;
identify, within the plurality of medical records, one or more documents associated with the patient and having a timestamp prior to a cutoff date such that documents including one or more dates expressed in relative terms are excluded from the identified one or more documents, the cutoff date being based on a predetermined buffer period before or after the date;
input unstructured information included in the one or more documents into a second machine learning model, the second machine learning model being trained using second training data to indicate dates associated with the condition;
generate one or more pseudo-documents for input into the second machine learning model, the one or more pseudo-documents accounting for one or more dates within the unstructured information included in the one or more documents;
determine, based on a second output from the second machine learning model, whether the patient is associated with the condition relative to the date; and
generate an output indicating whether the patient is associated with the condition and whether the patient is associated with the condition relative to the date.

2. The system of claim 1, wherein the condition includes a diagnosed metastatic site associated with the patient.

3. The system of claim 2, wherein the diagnosed metastatic site includes a brain metastasis.

4. The system of claim 1, wherein the condition includes a diagnosed condition of the patient.

5. The system of claim 1, wherein determining whether the patient is associated with the condition includes determining whether the patient has been tested for the condition.

6. The system of claim 1, wherein identifying the date includes identifying at least one of a start date or an end date for a line of treatment for the patient in association with the condition.

7. The system of claim 1, wherein identifying the date includes identifying a plurality of dates and wherein determining whether the patient is associated with the condition includes determining whether the patient is associated with the condition relative to each of the plurality of dates.

8. The system of claim 7, wherein the plurality of dates each include a start dates for a particular line of treatment for the patient in association with the condition.

9. The system of claim 1, wherein the at least one processor is further programmed to:
determine, using the first machine learning model and based on the unstructured information included in the plurality of medical records, whether each of the plurality of patients is associated with the condition; and
determine, using the second machine learning model and based on the unstructured information, whether each of the subset of the plurality of patients is associated with the condition relative to the date; and
wherein the output identifies a group of the subset of the plurality of patients associated with the condition relative to the date.

10. The system of claim 1, wherein the at least one processor is further programmed to transmit the output to at least one of a healthcare provider or a research entity.

11. A computer-assisted method for extracting patient information, the method comprising:
accessing a database storing a plurality of medical records associated with a plurality of patients;
inputting unstructured information included in the plurality of medical records into a first machine learning model, the first machine learning model being trained using first training data to identify patients associated with a condition;

identifying, based on a first output from the first machine learning model, a subset of the plurality of patients, the subset of the plurality of patients being associated with the condition;

identifying, based on an input by a user through a user interface, a date associated with a patient of the subset of the plurality of patients;

identifying, within the plurality of medical records, one or more documents associated with the patient and having a timestamp prior to a cutoff date such that documents including one or more dates expressed in relative terms are excluded from the identified one or more documents, the cutoff date being based on a predetermined buffer period before or after the date;

inputting unstructured information included in the one or more documents into a second machine learning model, the second machine learning model being trained using second training data to indicate dates associated with the condition;

generating one or more pseudo-documents for input into the second machine learning model, the one or more pseudo-documents accounting for one or more dates within the unstructured information included in the one or more documents;

determining, based on a second output from the second machine learning model, whether the patient is associated with the condition relative to the date; and generating an output indicating whether the patient is associated with the condition and whether the patient is associated with the condition relative to the date.

12. The method of claim 11, wherein the condition includes a diagnosed metastatic site associated with the patient.

13. The method of claim 11, wherein identifying the date includes identifying at least one of a start date or an end date for a line of treatment for the patient in association with the condition.

14. A non-transitory computer-readable medium storing instructions executable by at least one processor to perform a method, the method comprising:

accessing a database storing a plurality of medical records associated with a plurality of patients;

inputting unstructured information included in the plurality of medical records into a first machine learning model, the first machine learning model being trained using first training data to identify patients associated with a condition;

identifying, based on a first output from the first machine learning model, a subset of the plurality of patients, the subset of the plurality of patients being associated with the condition;

identifying, based on an input by a user through a user interface, a date associated with a patient of the subset of the plurality of patients;

identifying, within the plurality of medical records, one or more documents associated with the patient and having a timestamp prior to a cutoff date such that documents including one or more dates expressed in relative terms are excluded from the identified one or more documents, the cutoff date being based on a predetermined buffer period before or after the date;

inputting unstructured information included in the one or more documents into a second machine learning model, the second machine learning model being trained using second training data to indicate dates associated with the condition;

generating one or more pseudo-documents for input into the second machine learning model, the one or more pseudo-documents accounting for one or more dates within the unstructured information included in the one or more documents;

determining, based on a second output from the second machine learning model, whether the patient is associated with the condition relative to the date; and generating an output indicating whether the patient is associated with the condition and whether the patient is associated with the condition relative to the date.

15. The system of claim 1, wherein the one or more pseudo-documents are each associated with a document date matching the one or more dates within the unstructured information included in the one or more documents.

16. The system of claim 1, wherein the one or more pseudo-documents include information indicating a date as though text within the one or more pseudo-documents was written on the indicated date.

* * * * *